United States Patent [19]

Neel et al.

[11] Patent Number: 5,356,594

[45] Date of Patent: Oct. 18, 1994

[54] PORTABLE VOLATILE ORGANIC COMPOUND MONITORING SYSTEM

[75] Inventors: Edward M. Neel, Warwick, R.I.; John F. Dwinell, Foxboro; Michael T. Nemergut, III, Westborough, both of Mass.

[73] Assignee: Thermo Environmental Instruments Inc., Franklin, Mass.

[21] Appl. No.: 846,272

[22] Filed: Mar. 3, 1992

[51] Int. Cl.$^5$ ............................................. G01N 21/72
[52] U.S. Cl. ........................................ 422/54; 422/62; 422/83; 436/3; 364/497; 364/551.01; 73/31.02; 73/31.05
[58] Field of Search ................ 422/54, 83, 94, 95.98, 422/62, 67; 250/288; 436/3; 364/497, 499, 550, 551.01; 73/25.03, 25.05, 31.02, 31.03, 31.05

[56] References Cited

U.S. PATENT DOCUMENTS

| | | | |
|---|---|---|---|
| 4,360,798 | 11/1982 | Swartz | 340/146.3 AG |
| 4,528,159 | 7/1985 | Liston | 422/65 |
| 4,897,532 | 1/1990 | Swartz | 235/467 |
| 5,047,617 | 9/1991 | Shepard | 235/467 |
| 5,099,437 | 3/1992 | Weber | 364/550 |
| 5,116,764 | 5/1992 | Annino et al. | 436/161 |

OTHER PUBLICATIONS

Thermo Environmental Instruments, Inc., *Model 580B Organic Vapor Meter Data Logger*, 4 pages (1989).
Thermo Environmental Instruments, Inc., *Model 580S Intrinsically Safe Organic Vapor Meter data Logger*, 2 pages (1991).

Primary Examiner—David A. Redding
Attorney, Agent, or Firm—Fish & Richardson

[57] ABSTRACT

A portable (handheld) volatile organic compound monitoring system for monitoring, for fugitive emissions, a device that includes a coded identification tag. The system includes a housing, a tag reader, analysis chamber structure, a sample probe coupled to the analysis chamber, and pump structure for drawing a gas sample to be analyzed through the sample probe into the analysis chamber. Ionization apparatus is coupled to the analysis chamber for ionizing a gas sample drawn into the analysis chamber from the device being monitored, and a sensor responsive to ionized gas in the chamber produces an output signal as a function of an ionization characteristic of the ionized gas. First storage stores a plurality of response factors as a function of various types of volatile organic compounds to be monitored, second storage stores tag information read by the tag reader, and circuitry responsive to tag information stored in the second storage selects a response factor from the first storage. Microprocessor apparatus responsive to tag information, selected response factor information, and the sensor output signal produces an output indicative of volatile organic compound (VOC) concentration at the monitored device.

14 Claims, 2 Drawing Sheets

PORTABLE VOLATILE ORGANIC COMPOUND MONITORING SYSTEM

This invention relates to monitoring systems and more particularly to systems for monitoring volatile organic compounds and the like.

It is desirable to monitor process components such as valves, pumps, compressors, pressure relief devices and the like in chemical manufacturing operations, petroleum refineries and the like for leaks of volatile organic compounds. Devices to be monitored are frequently located both in the field and in process plants in relatively inaccessible locations, and often the environment is harsh and corrosive. The Environmental Protection Agency (EPA) has promulgated regulations concerning the control of fugitive emissions, and the majority of existing systems for monitoring such emissions in accordance with EPA regulations are very labor intensive. In a typical system, one person operates a detection device and makes leak measurements and a second person records in a notebook individual data measurements together with information on the particular device being monitored.

In accordance with one aspect of the invention, there is provided a portable volatile organic compound monitoring system for monitoring, for fugitive emissions, a device that includes a coded identification tag. The system includes a housing, a tag reader, analysis chamber structure, a sample probe coupled to the analysis chamber, ionization apparatus coupled to the analysis chamber for ionizing a gas sample drawn into the analysis chamber through the sample probe from the device being monitored, a sensor responsive to ionized gas in the chamber for producing an output signal as a function of an ionization characteristic of the ionized gas, first storage for storing a plurality of response factors as a function of various types of volatile organic compounds to be monitored, second storage for storing tag information read by the tag reader, circuitry responsive to tag information stored in the second storage for selecting a response factor from the first storage, and microprocessor apparatus responsive to tag information, selected response factor information, and the sensor output signal for producing an output indicative of volatile organic compound (VOC) concentration at the monitored device.

In one particular embodiment, the ionization apparatus coupled to the analysis chamber is of the photoionization type and includes jet electrode structure through which a gas sample from the sample probe is flowed, guard electrode structure and collector electrode structure coupled to the analysis chamber, and a source of ultraviolet radiation for ionizing gas in the sample chamber. In another embodiment, the ionization apparatus is of the flame type and includes a conduit for supplying a gas sample from the probe to the analysis chamber, a collector electrode, an ignitor, and a temperature sensor. The outlet port of a fuel supply tube, the collector electrode, ignitor, temperature sensor and the outlet port of the gas sample supply conduit are disposed in the analysis chamber, the fuel supplied through the tube being ignited by the ignitor to ionize the gas sample for sensing by the collector electrode. Response factors stored in the first memory include factors for aromatic compounds, unsaturated compounds, saturated compounds, ketones, and alcohols. Other stored parameters include a leak limit value (the maximum allowable concentration in parts per million (PPM) before repair is required); an operating mode (max hold or normal, for example); an averaging time (in seconds); and a background subtraction value (to account for factors such as methane normally found in air).

In a particular embodiment, the tag is a label with an aluminum base, a bar code on the aluminum base and a Teflon (PTFE) coating that provides a transparent protective layer over the bar code. The tag reader may include a laser that provides an output beam, scanner mirror structure for oscillating the output beam to scan a bar code, a reader sensor, and second mirror structure for reflecting radiation from the scanned bar code to the reader sensor.

Systems in accordance with the invention provide comprehensive fugitive emission monitoring with portable integrated sampling-tag reader units for operation by a single individual and that enable correlation of devices being monitored and data from those devices, as well as organized data for further analysis and data manipulation.

Other features and advantages of the invention will be seen as the following description of particular embodiments progresses, in conjunction with the drawings, in which:

DESCRIPTION OF PARTICULAR EMBODIMENTS

Figure 1:
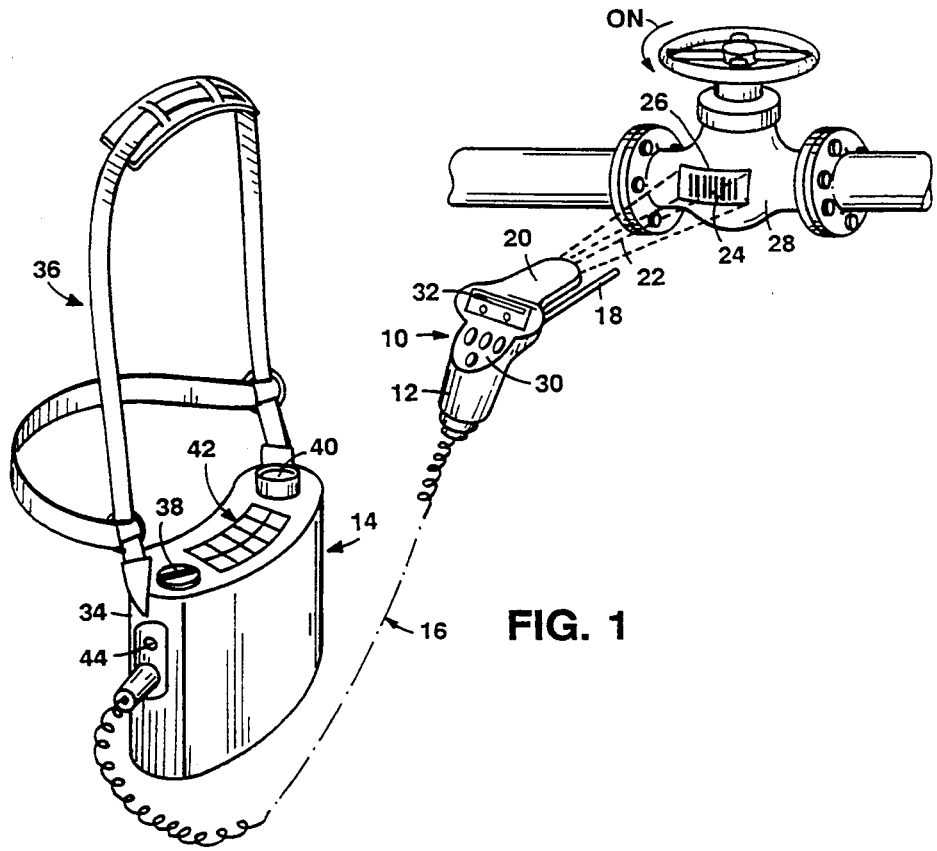
FIG. 1 is a diagrammatic perspective view of a monitoring system in accordance with the invention that is shown in use for monitoring a coupling flange in a chemical process installation.

With reference to FIG. 1, there is shown a fugitive emissions monitoring system that includes handheld probe-reader unit 10 with handle portion 12. Unit 10 connected to analyzer and data storage unit 14 by umbilical cord 16. Fixed to and protruding forwardly from unit 10 is sample probe 18, and positioned above probe 18 is housing 20 of a scanner type label reader that generates a beam 22 of radiation for reading bar code 24 on label 26 that is associated with a component to be monitored such as valve 28. Label 26 has an aluminum base with bar code 24 on that base. Teflon (PTFE) coating applied over bar code 24 provides a transparent protective layer over bar code 24 which resists adherence of obscuring material such as paint.

Unit 10 includes an array of control buttons 30 and a two line alphanumeric LCD display 32. In a monitoring mode, the top line of display 32 indicates a maximum reading and the bottom line indicates the current PPM reading in the region where the tip of probe 18 is located, the top line of the display being updated whenever a new maximum is sensed. Analyzer unit 14 includes housing 34 to which carrying straps 36 are attached which permit the analyzer unit 14 to be supported/worn on the shoulder and around the waist of a user. Disposed within housing 34 are ionization apparatus of the flame type with a hydrogen fuel supply, a pump (see FIG. 2) for drawing a sample into the probe 18 and then through a conduit in umbilical cord 16 into the flame ionization apparatus, and data processing apparatus that includes a microprocessor and data storage and that communicates with control buttons 30 and display 32 over umbilical cord 16. On the upper surface of housing 34 are pressure gage 38, hydrogen fuel off-/on control 40 and control keyboard 42. An RS232 computer connection 44 is provided on the rear surface of housing 34 adjacent the connection for umbilical cord 16.

In an alternate embodiment, the monitoring system is housed in a single portable hand-held unit with a sample probe 18 protruding from a front face of the housing and a label reader of the contact wand type releasably mounted on the housing by means of a bracket and connected to that housing via a cable. In that embodiment, the sample analyzer is of the photoionization type.

Figure 2:
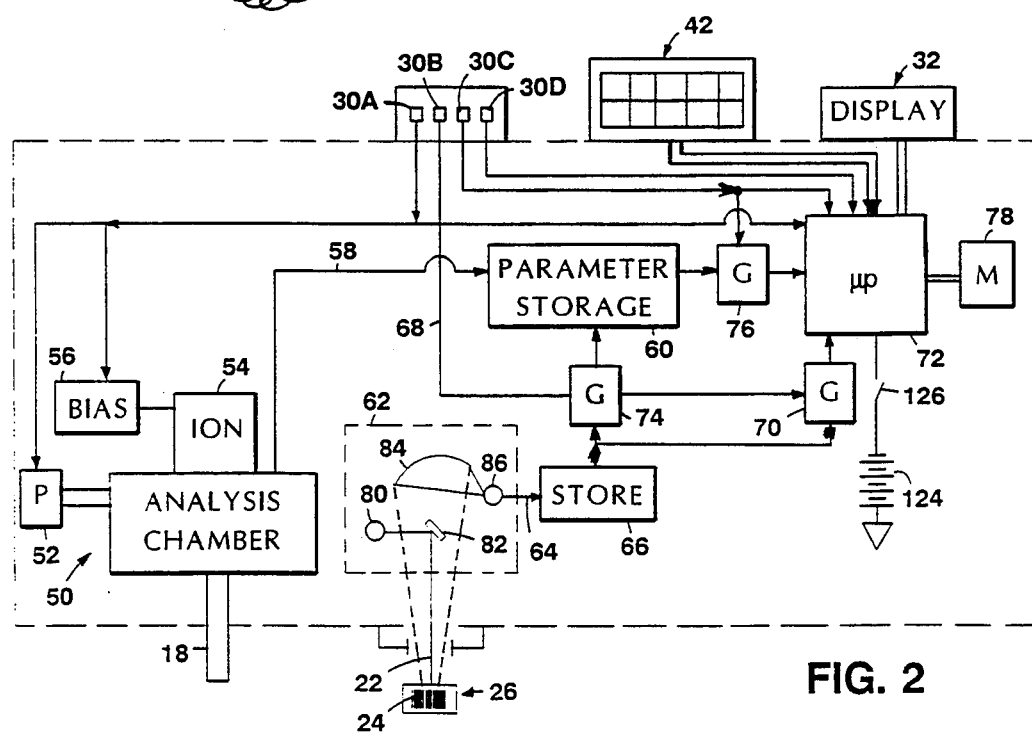
FIG. 2 is a block diagram of components of a system in accordance with invention.

A block diagram of the monitoring system is shown in FIG. 2. That system includes analysis chamber assembly 50 to which sampling probe 18 and pump 52 are connected, probe 18 being connected to chamber 50 by a conduit in umbilical cord 16 in the flame ionization system of FIG. 1 and housed in the unit 10 on which sampling probe 18 is mounted in a photoionization type system. Also coupled to analysis chamber 50 is ionization device 54 to which a bias voltage is applied from source 56 and which applies an output from chamber 50 over line 58 to parameter storage 60.

Mounted in reader housing 20 is sensor circuitry 62 whose output is applied over line 64 to storage 66 and which stored output in response to a signal to key 30B over line 68 is in turn applied through gate 70 to microprocessor 72 and through gate 74 to parameter storage 60 for selection of the group of stored parameters associated with the sensed tag code 26. In a particular system, those parameters include a leak limit value (the maximum allowable PPM concentration before repair of the monitored device is required); a response factor (correlating the volatile organic compound of interest to a calibrating gas); an operating mode (max hold or normal, for example); an averaging time (in seconds); and a background subtraction value (to account for factors such as methane normally found in air). Each such group of parameters is associated with a particular device to be monitored and determines how the system will operate at the device identified by the sensed bar code. These control parameter factors may be saved to disk and selected parameters downloaded to the monitor instrument according to a predetermined route of devices to be monitored that is selected before the operator begins the route.

An analyzer output signal on line 58 is applied through parameter storage 60 and gate 76 for modification in accordance with the selected response factor parameter by microprocessor 72 as a compensated VOC signal and the processed data is stored in data store 78 correlated with identification of the monitored device 28, its location, time of measurement, etc. Storage memory 78 may, for example, have a capacity for storing up to 700 individual sample measurements.

As indicated above, reader circuitry 62 may be of the scanning contact wand which uses an infrared illumination mechanism to read the bar code 24 on tag 26 or of the laser scanner type as diagrammatically shown in FIG. 2. The bar code tag 26 is often situated in relatively inaccessible locations associated with various process component plumbing. The laser scanner reader circuitry shown in FIG. 2 includes laser 80 and scanner mirror 82 that directs output beam 22 from housing 20 to scan bar code 24. Radiation in incident beam 22 is returned from bar code 24 and reflected by spherical mirror 84 to probe sensor 86 whose output is applied over line 64 to store 66. Reader operation may be initiated by depression of a control key 30 or by other suitable means such as a proximity sensor.

Figure 3:
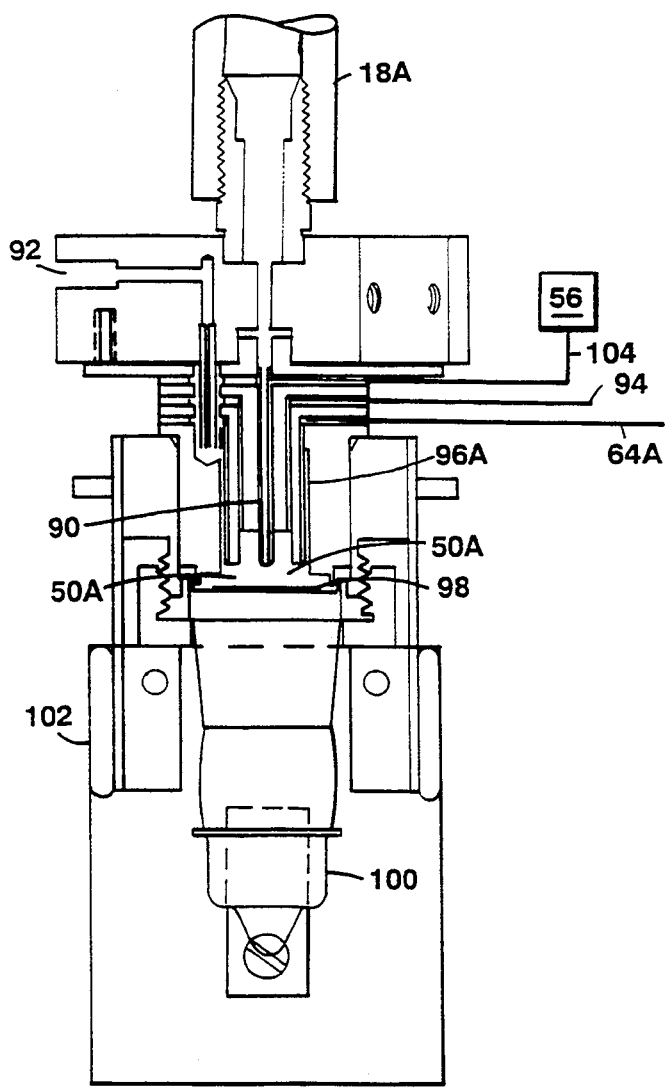
FIG. 3 is a diagram of a photoionization detector for use in the system of FIG. 2.
Figure 4:
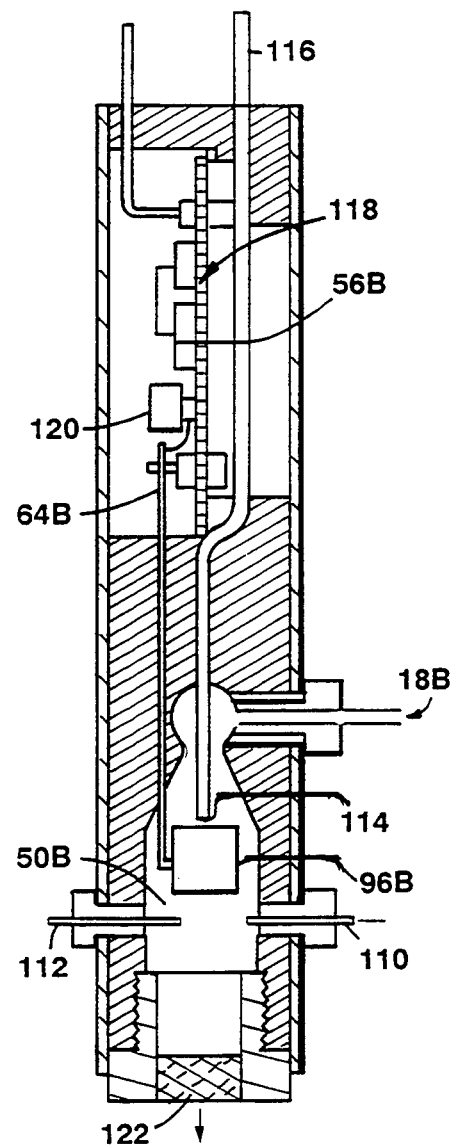
FIG. 4 is a diagram of a flame ionization detector employed in the system of FIG. 1.

The gas ionization apparatus assembly may be of the photoionization type shown in FIG. 3 or of the flame ionization type shown in FIG. 4. Components of similar function are identified with numerals having the suffix "A" in FIG. 3 and the suffix "B" in FIG. 4. The photoionization assembly includes chamber region 50A to which sample probe 18A is coupled by jet electrode 90 and through which the sample in probe 18A is flowed in response to pump 52 that is coupled to outlet 92. Guard electrode 94 and collector electrode 96 are also coupled to analysis chamber 50A. Forming one wall of chamber 50A is window 98 of ultraviolet (UV) lamp 100 that is energized by power supply 102. A bias voltage from source 56 is applied over line 104 to jet electrode 90 to aid in collection of ions. As a result of impingement of UV energy from lamp 100 on the gas sample in chamber 50A, positively charged ions and free electrons are produced. The jet electrode 90 is negative relative to collector electrode 96A where the electrons are collected. Between jet electrode 90 and collector electrode 96A is guard electrode 94 whose function is to eliminate surface currents which could flow between the two active electrodes 90, 96A.

An ionization system of the flame type is shown in FIG. 4. In that system the gas sample is applied from the probe 18 through inlet 18B to analysis chamber 50B. Disposed in chamber 50B is collector electrode 96B, ignitor 110, thermocouple temperature sensor 112 and the outlet port 114 of hydrogen fuel supply tube 116. Electronics are mounted on PC board 118 and include electrometer circuitry 120, and circuitry 56B for applying a bias voltage to collector electrode 96B. The combustion products from the gas sample being analyzed are exhausted from chamber 50B through frit membrane 122. The output signal from collector electrode 96B is applied on line 58 to parameter storage 60 (FIG. 2).

In system use, battery 124 is connected to power the system by switch 126 controlled by key 42A. Pressing on/off button 30A causes microprocessor 72 to energize the ionization system 54. In the case of the photoionization system shown in FIG. 3, microprocessor 72 energizes pump 52, the high voltage supply 102 and lamp 100. Once lamp 100 is lighted, a PPM indication appears on display 32. In the case of the flame ionization system shown in FIG. 4, microprocessor 72 energizes pump 52, opens a valve to commence flow of hydrogen fuel to port 114 and energizes ignitor 110 to initiate an ionization flame in analysis chamber 50B.

The operator approaches the process component 28 to be monitored such as the flange of a valve. Reading of device type and location data is initiated for entry into storage 66 via reader apparatus 62 from the bar code 24 on label 26 in response to actuation of the reader circuitry by a proximity sensor or by depression of a control button 30. Microprocessor control signals may be entered via keyboard 42. Pressing parameter select button 30B causes the data from storage 66 to select the related parameters from storage 60 via gate 74 and the device identification to be entered into microprocessor 72 via gate 70.

After monitor control button 30C is depressed, the sample probe 18 is maneuvered around the flange or similar region of the process component 28 being monitored, a gas sample is drawn through probe 18 into the analysis chamber 50 and ionized, analyzer outputs from the collector electrode 96 over line 58 are read through parameter storage 60 and gate 76 into microprocessor 72, and a compensated concentration reading is displayed at display 32. When a maximum concentration reading associated with the component 28 is observed, store button 30D is depressed, causing the compensated reading to be stored by microprocessor 72 in data store 78 along with the time, date and location identification data and concurrently releasing monitor button 30C. If indicated, repair may be undertaken and the device 28 then rechecked by a similar monitoring and storage sequence.

The operator then proceeds to the next component to be monitored on the route and repeats the routine in similar fashion. Upon completion of a prescribed survey route, the leak measurement data may be downloaded to a printer, or to a personal computer or the like for storage and/or subsequent data manipulation.

Optional additional features may include aspects such as reread capability for situations in which an exceedance (violation) measurement is encountered and repair is attempted; report identification of any missed component identification tags; the ability to measure and record a background measurement for automatic subtraction from a fugitive emission measurement; calculation and reporting of mass emission rates (KG/hour) from leak concentration data; and programming of a prescribed survey route that allows the system to prompt the operator through a designated leak survey route.

While particular embodiments of the invention have been shown and described, various modifications will be apparent to those skilled in the art, and therefore, it is not intended that the invention be limited to the disclosed embodiments, or to details thereof, and departures may be made therefrom within the spirit and scope of the invention.

What is claimed is:

1. A portable volatile organic compound monitoring system for monitoring a device that includes a coded identification tag, said system comprising housing structure, tag reader structure in said housing structure, and analyzer and data storage unit, said unit comprising:

means defining an analysis chamber, a sample probe fixed to said housing structure and coupled via a conduit to said analysis chamber;
   means for drawing a gas sample to be analyzed through said sample probe into said analysis chamber;
   ionization apparatus coupled to said analysis chamber for ionizing a gas sample drawn into said analysis chamber through said sample probe from the device being monitored;
   sensor apparatus responsive to ionized gas in said analysis chamber for producing an output signal as a function of an ionization characteristic of the ionized gas;
   first storage means for storing a plurality of response factors as a function of various types of volatile organic compounds to be monitored;
   second storage means for storing tag information read by said tag reader structure;
   circuitry means responsive to tag information stored in said second storage means for selecting a response factor from said first storage means; and
   microprocessor apparatus responsive to response factor information from said first storage means selected in response to said stored tag information from said second storage means and said sensor apparatus output signal for producing an output indicative of volatile organic compound concentration at the monitored device.

2. The system of claim 1 wherein said ionization apparatus is of the flame type.

3. The system of claim 1 wherein said response factors include factors for aromatic compounds, unsaturated compounds, saturated compounds, ketones, and alcohols.

4. The system of claim 1 wherein said tag reader structure includes a laser that provides an output beam, scanner mirror structure for oscillating said output beam to scan a bar code, a reader sensor, and second mirror structure for reflecting radiation from said scanned bar code to said reader sensor.

5. The system of claim 1 wherein said ionization apparatus includes a conduit for supplying a gas sample from said probe to said analysis chamber, a collector electrode, an ignitor, a temperature sensor and the outlet port of a fuel supply tube, said collector electrode, ignitor, temperature sensor and tube outlet port being disposed in said analysis chamber, fuel supplied through said fuel supply tube being adapted to be ignited by said ignitor to ionize said gas sample for sensing by said collector electrode.

6. The system of claim 1 wherein said system further includes a battery for powering said microprocessor apparatus.

7. A portable volatile organic compound monitoring system for monitoring a device that includes a coded identification tag, said system comprising housing structure, tag reader structure positioned and arranged as an integral part of said housing structure, and analyzer and data storage unit, said unit comprising:

means defining an analysis chamber, a sample probe coupled via a conduit to said analysis chamber;
   means for drawing a gas sample to be analyzed through said sample probe into said analysis chamber;
   ionization apparatus coupled to said analysis chamber for ionizing a gas sample drawn into said analysis chamber through said sample probe from the device being monitored;
   sensor apparatus responsive to ionized gas in said analysis chamber for producing an output signal as a function of an ionization characteristic of the ionized gas;
   first storage means for storing a plurality of response factors as a function of various types of volatile organic compounds to be monitored,
   second storage means for storing tag information read by said tag reader structure;
   circuitry means responsive to tag information stored in said second storage means for selecting a response factor from said first storage means; and
   microprocessor apparatus responsive to response factor information from said first storage means selected in response to said stored tag information from said second storage means and said sensor apparatus output signal for producing an output indicative of volatile organic compound concentration at the monitored device.

8. A portable volatile organic compound monitoring system for monitoring a device that includes a coded identification tag, said system comprising a handheld probe-reader unit with a handle portion and tag reader structure, analyzer and data storage unit, said unit comprising:
- means defining an analysis chamber, a sample probe coupled via a conduit to said analysis chamber;
- means for drawing a gas sample to be analyzed through said sample probe into said analysis chamber;
- ionization apparatus coupled to said analysis chamber for ionizing a gas sample drawn into said analysis chamber through said sample probe from the device being monitored;
- sensor apparatus responsive to ionized gas in said analysis chamber for producing an output signal as a function of an ionization characteristic of the ionized gas;
- first storage means for storing a plurality of response factors as a function of various types of volatile organic compounds to be monitored;
- second storage means for storing tag information read by said tag reader structure;
- circuitry means responsive to tag information stored in said second storage means for selecting a response factor from said first storage means; and
- microprocessor apparatus connected to said probe-reader unit, said microprocessor apparatus being responsive to response factor information from said first storage means selected in response to said stored tag information from said second storage means and said sensor apparatus output signal for producing an output indicative of volatile organic compound concentration at the monitored device.

9. The system of claim 8 wherein said probe-reader unit includes a sample probe fixed to and protruding forwardly from said probe-reader unit and a scanner reader that generates a beam of radiation for reading a bar code on a tag that is associated with a component to be monitored.

10. The system of claim 9 wherein said first storage means stores a plurality of parameters including leak limit values; said response factors; operating modes; averaging times; and background subtraction values.

11. The system of claim 8 wherein said tag reader structure includes a laser that provides an output beam, scanner mirror structure for oscillating said output beam to scan a bar code, a reader sensor, and second mirror structure for reflecting radiation from a scanned bar code to said reader sensor.

12. A portable volatile organic compound monitoring system for monitoring a device that includes a coded identification tag, said system comprising a handheld probe-reader unit with a handle portion and an analyzer and data storage unit connected to said probe-reader unit, said probe-reader unit including a sample probe fixed to and protruding forwardly from said probe-reader unit and a reader that generates a beam of radiation for reading a bar code on a tag that is associated with a component to be monitored,
- said analyzer including means defining an analysis chamber,
- means for drawing a gas sample to be analyzed through said sample probe into said analysis chamber,
- ionization apparatus coupled to said analysis chamber for ionizing a gas sample drawn into said analysis chamber through said sample probe from the device being monitored,
- sensor apparatus responsive to ionized gas in said analysis chamber for producing an output signal as a function of an ionization characteristic of the ionized gas;
- said data storage unit including first storage means for storing a plurality of response factors as a function of various types of volatile organic compounds to be monitored, and second storage means for storing tag information read by said reader,
- circuitry means responsive to tag information stored in said second storage means for selecting a response factor from said first storage means, and
- microprocessor apparatus responsive to response factor information from said first storage means selected in response to said stored tag information from said second storage means and said sensor apparatus output signal for producing an output indicative of volatile organic compound concentration at the monitored device.

13. The system of claim 12 wherein said first storage means stores a plurality of parameters including leak limit values; said response factors; operating modes; averaging times; and background subtraction values; said response factors including factors for aromatic compounds, unsaturated compounds, saturated compounds, ketones, and alcohols.

14. The system of claim 13 wherein said ionization apparatus is of the flame type, and includes a conduit for supplying a gas sample from said sample probe to said analysis chamber, a collector electrode, an ignitor, a temperature sensor and a fuel supply tube, said collector electrode, ignitor, temperature sensor and outlet ports of said conduit and said fuel supply tube being disposed in said analysis chamber, the fuel supplied through said fuel supply tube being adapted to be ignited by said ignitor to ionize said gas sample for sensing by said collector electrode.

* * * * *